United States Patent
Ueki et al.

(10) Patent No.: US 9,354,245 B2
(45) Date of Patent: May 31, 2016

(54) PIPETTE TIP SET TO BE USED IN DISPENSING DEVICE AND METHOD FOR PERFORATING REAGENT CARTRIDGE FILM USING SAME

(71) Applicant: TOPPAN PRINTING CO., LTD., Tokyo (JP)

(72) Inventors: Tatsuya Ueki, Tokyo (JP); Hiroyuki Kuroki, Tokyo (JP); Eiji Kawata, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 0 days.

(21) Appl. No.: 14/279,898

(22) Filed: May 16, 2014

(65) Prior Publication Data

US 2014/0248704 A1 Sep. 4, 2014

Related U.S. Application Data

(63) Continuation of application No. PCT/JP2012/007547, filed on Nov. 22, 2012.

(30) Foreign Application Priority Data

Nov. 25, 2011 (JP) .................................. 2011-257988

(51) Int. Cl.
  *G01N 35/10* (2006.01)
  *G01N 35/00* (2006.01)
  (Continued)

(52) U.S. Cl.
  CPC .......... *G01N 35/1079* (2013.01); *B01L 3/0275* (2013.01); *B01L 2300/0672* (2013.01);
  (Continued)

(58) Field of Classification Search
  CPC .............. G01N 2035/1025; G01N 2035/1018; G01N 1/38; G01N 35/1016; G01N 35/1004; G01N 1/10; Y10T 436/119163; Y10T 436/11; Y10T 436/00
  USPC ........................................................... 436/54
  See application file for complete search history.

(56) References Cited

U.S. PATENT DOCUMENTS

| 4,721,137 A | 1/1988 | Müller |
| 5,130,254 A * | 7/1992 | Collier ............... G01N 35/1079 |
| | | 422/568 |

(Continued)

FOREIGN PATENT DOCUMENTS

| EP | 2 439 537 A1 | 4/2012 |
| EP | 2 453 219 A1 | 5/2012 |

(Continued)

OTHER PUBLICATIONS

International Search Report mailed Feb. 12, 2013 in corresponding International Patent Application No. PCT/JP2012/007547.

*Primary Examiner* — Christine T Mui

(57) ABSTRACT

A method which allows easy perforation of a film covering a well of a reagent cartridge which is set to a dispensing device is provided. A pipette tip set to be used in a dispensing device of an automatic analyzer together with a reagent cartridge in which a reagent for biochemical analysis is enclosed, includes: a dispensing pipette tip for dispensing the reagent enclosed in the reagent cartridge; a perforating pipette tip having a leading end surface inclined relative to a central axis thereof; and a rack configured to store the dispensing pipette tip and the perforating pipette tip together.

5 Claims, 7 Drawing Sheets

(51) Int. Cl.
  *G01N 1/38* (2006.01)
  *B01L 3/02* (2006.01)
  *G01N 35/04* (2006.01)

(52) U.S. Cl.
  CPC .. *G01N2035/0436* (2013.01); *G01N 2035/103* (2013.01); *G01N 2035/1025* (2013.01); *Y10T 436/11* (2015.01); *Y10T 436/119163* (2015.01)

(56) References Cited

U.S. PATENT DOCUMENTS

| | | | |
|---|---|---|---|
| 5,315,887 A | 5/1994 | Heitel | |
| 5,413,000 A | 5/1995 | Stark et al. | |
| 7,318,911 B2* | 1/2008 | Smith | 422/513 |
| 2001/0039058 A1* | 11/2001 | Iheme et al. | 436/180 |
| 2007/0148052 A1 | 6/2007 | Hiramatsu et al. | |
| 2009/0155123 A1 | 6/2009 | Williams et al. | |
| 2009/0263904 A1 | 10/2009 | Clinton et al. | |
| 2011/0171670 A1 | 7/2011 | Miyashita | |
| 2012/0122231 A1 | 5/2012 | Tajima | |
| 2012/0184025 A1 | 7/2012 | Kawata et al. | |

FOREIGN PATENT DOCUMENTS

| | | |
|---|---|---|
| JP | 62-100662 | 5/1987 |
| JP | 4-500732 | 2/1992 |
| JP | 5-87568 | 11/1993 |
| JP | 6-57427 | 8/1994 |
| JP | 11-183484 | 7/1999 |
| JP | 2007-3350 | 1/2007 |
| JP | 2011-128123 | 6/2011 |
| JP | 2011-518323 | 6/2011 |
| TW | 201103499 | 2/2011 |
| WO | WO 2011/004653 A1 | 1/2011 |
| WO | WO 2011/040504 A1 | 4/2011 |

* cited by examiner

Example 3

Example 4

PIPETTE TIP SET TO BE USED IN DISPENSING DEVICE AND METHOD FOR PERFORATING REAGENT CARTRIDGE FILM USING SAME

CROSS-REFERENCE TO RELATED APPLICATIONS

This application is a continuation application of PCT/JP2012/007547 filed Nov. 22, 2012 and claims foreign priority benefit of Japanese Application No. 2011-257988 filed Nov. 25, 2011 in the Japanese Intellectual Property Office, the contents of which are incorporated herein by reference.

BACKGROUND

1. Field

The present disclosure relates to a pipette tip set to be used in a dispensing device and a method for easily perforating a film covering a reagent cartridge by using the same.

2. Description of the Related Art

In recent years, in the life science field, the possibility is suggested that sensitivity to a pharmaceutical preparation is predictable by extracting a nucleic acid from a specimen collected from a patient and detecting a mutation in a gene such as single nucleotide polymorphism.

A process of extracting a nucleic acid from a specimen as described above is generally performed by using an automatic analyzer. Reagents used in the automatic analyzer are often stored in wells provided in a storage member called a cartridge. A film is often attached to such a cartridge so as to cover the wells for the purpose of preventing volatilization of the reagents which are put within the wells, incorporation of foreign matter from the outside, and the like.

Thus, when the reagent put within the well is used, before the reagent within the well is sucked with a dispensing pipette tip, it is necessary to peel off the film covering the well or perforate the film. In the former case, it is conceivable that the film is previously manually peeled off, but it requires operator's time and effort and thus the test efficiency is deteriorated. In the latter case, it is conceivable that the film is pierced by using the dispensing pipette tip, but the film may not be successfully pierced and a leading end of the dispensing pipette tip may be bent, or even when the film is successfully pierced, there is the risk that a portion of the pierced film drops into the well.

In order to solve the above-described problems that arise when the film is previously perforated, in Japanese Laid-Open Patent Publication No. 2007-3350, a pin is additionally mounted at a leading end of a pipette tip and a film is perforated by using the pin.

However, in the perforating method described in Japanese Laid-Open Patent Publication No. 2007-3350, time and effort to mount the dedicated pin at the leading end of the pipette tip and the cost required to produce the pin are problems.

SUMMARY

The present disclosure provides a pipette tip set which allows easy perforation of a film covering a well of a reagent cartridge which is set to an automatic analyzer; and a perforating method using the same.

The present disclosure is directed to a pipette tip set to be used in a dispensing device of an automatic analyzer together with a reagent cartridge in which a reagent for biochemical analysis is enclosed. The pipette tip set includes: a dispensing pipette tip for dispensing the reagent enclosed in the reagent cartridge; a perforating pipette tip having a leading end surface inclined relative to a central axis thereof; and a rack configured to store the dispensing pipette tip and the perforating pipette tip together.

In addition, the present disclosure is directed to a perforating method for perforating a film covering a well provided in a reagent cartridge by using a dispensing device including: a dispensing head configured to suck and discharge a liquid; and a stage configured to support the reagent cartridge in which a reagent for biochemical analysis is enclosed. In the perforating method, a perforating pipette tip having a leading end surface inclined relative to a central axis thereof is mounted on the dispensing head; a leading end of the perforating pipette tip mounted on the dispensing head is disposed perpendicularly above the film; and the dispensing head is moved downward to stick the leading end of the perforating pipette tip into a film to form a hole in the film.

According to the present disclosure, since the perforating pipette tip has the leading end surface inclined relative to the central axis thereof, it is possible to easily perforate the film covering the well of the cartridge.

These and other objects, features, aspects and advantages of the present disclosure will become more apparent from the following detailed description of the present disclosure when taken in conjunction with the accompanying drawings.

DETAILED DESCRIPTION

In the following description, for convenience of explanation, a direction is specified by using a three-dimensional orthogonal coordinate system, an X axis and a Y axis are set as axes parallel to a horizontal plane, and a Z axis is set as an axis perpendicular to the horizontal plane.

<1. Configuration of Nucleic Acid Analyzer>

Figure 1:
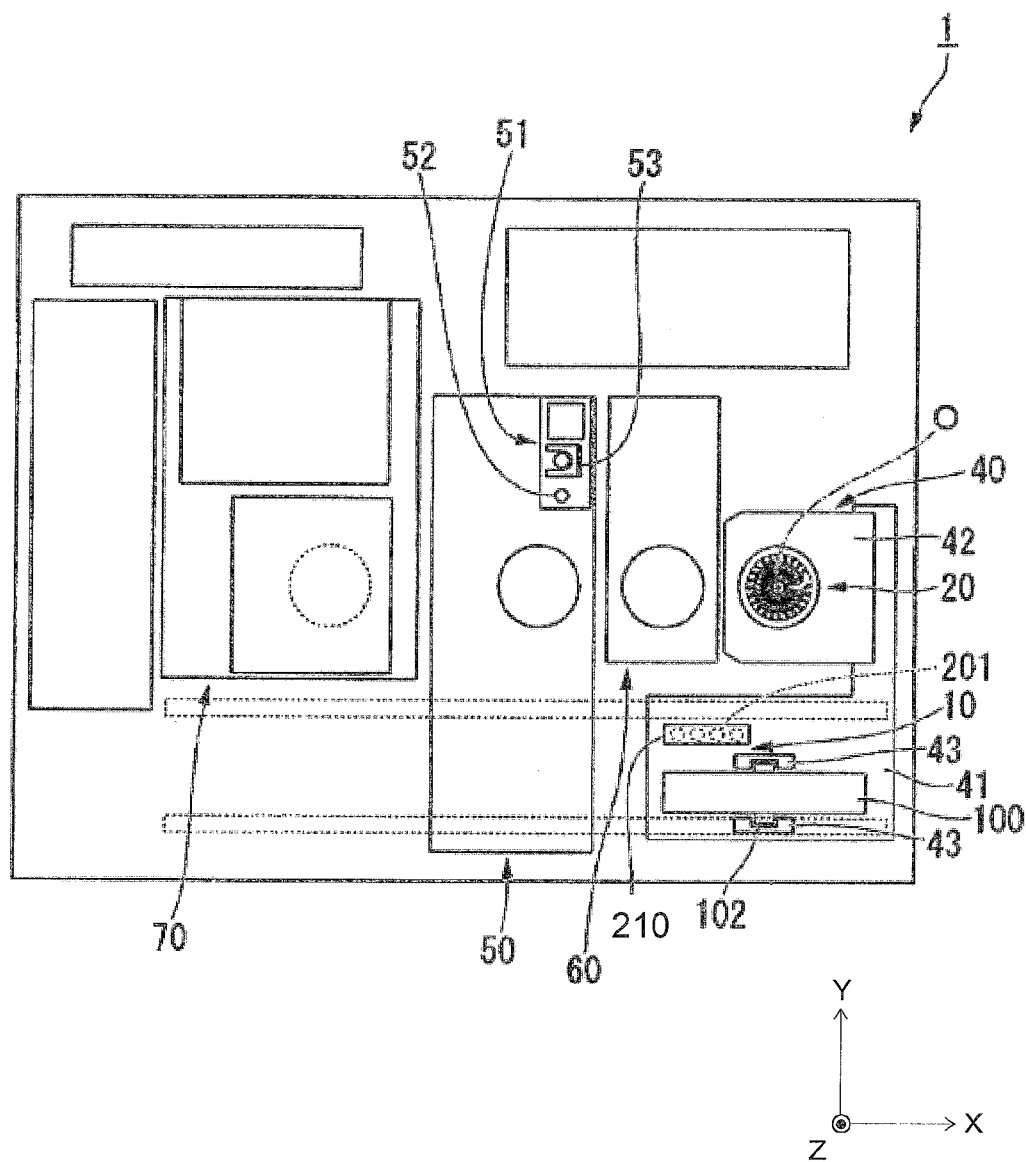
FIG. 1 is a top view showing a schematic configuration of a nucleic acid analyzer according to an embodiment.

FIG. 1 is a top view showing a schematic configuration of a nucleic acid analyzer according to an embodiment.

The nucleic acid analyzer 1 includes a test sample introduction portion 40, a purification treatment portion 50, a centrifugal liquid feed portion 60, and an analysis portion 70. A nucleic acid purification kit 10 destroys cells contained in a test sample such as a biological sample and causes a nucleic acid contained in the cells to be adsorbed on a carrier to separate and purify the nucleic acid. A nucleic acid analysis chip 20 performs a biochemical reaction on the nucleic acid purified by the nucleic acid purification kit 10. The nucleic acid purification kit 10 and the nucleic acid analysis chip 20 are disposed at the test sample introduction portion 40. The test sample introduction portion 40 includes a stage 41 which is movable in a Y axis direction by a transfer mechanism which is not shown; and an analysis chip holder 42 for mounting the nucleic acid analysis chip 20 thereon. An engaged portion 43 for fixing and positioning a reagent cartridge 100 is provided on the stage 41. The reagent cartridge 100 is mounted on the stage 41 by using the engaged portion 43. The purification treatment portion 50 performs an operation of extracting a nucleic acid from a test sample by using the nucleic acid purification kit 10. The purification treatment portion 50 includes a robot hand 51, a dispensing head 52, and a pressurizing portion 53. It should be noted that the details of the purification treatment portion 50 will be described later. The centrifugal liquid feed portion 60 is a mechanism which rotates the nucleic acid analysis chip 20 about a central axis O. In addition, the analysis portion 70 analyzes a nucleic acid within a reaction vessel (not shown) of the nucleic acid analysis chip 20.

<2. Details of Nucleic Acid Purification Kit>

Figure 2:
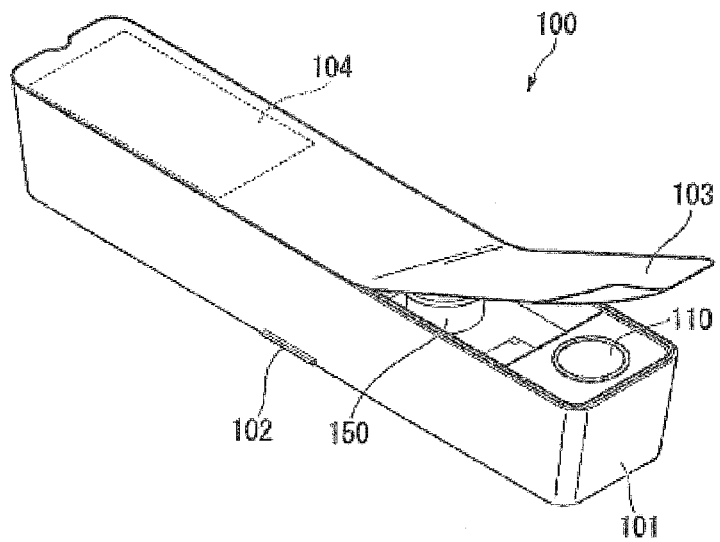
FIG. 2 is a perspective view showing the configuration of a nucleic acid purification kit.
Figure 3:
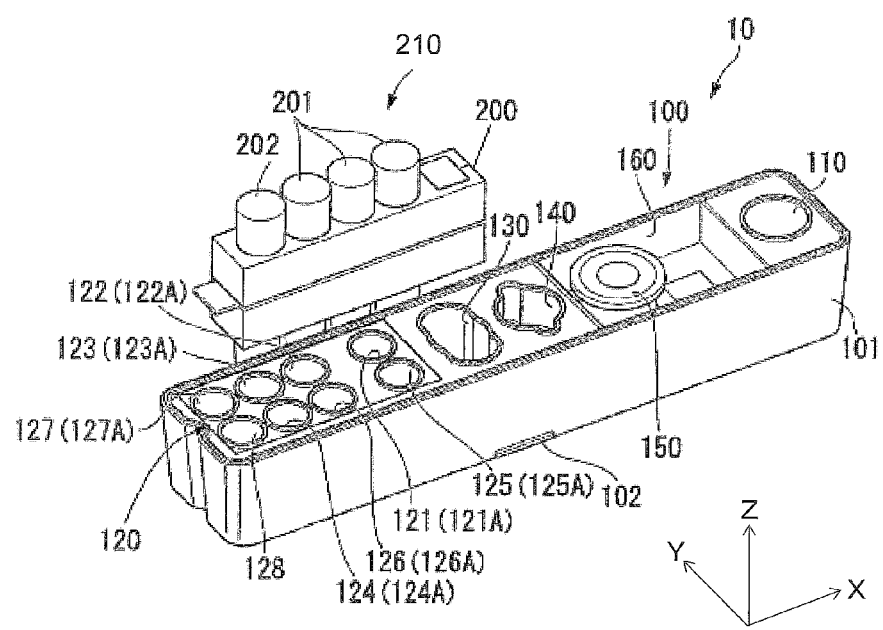
FIG. 3 is a perspective view showing the configuration of the nucleic acid purification kit.

FIGS. 2 and 3 are perspective views showing the configuration of the nucleic acid purification kit.

The nucleic acid purification kit 10 includes: the reagent cartridge 100 in which reagents for extracting a nucleic acid from a test sample, and the like are contained; and a pipette tip kit 210. The pipette tip kit 210 includes: a plurality of dispensing pipette tips 201 for dispensing a liquid; a perforating pipette tip 202; and a pipette tip rack 200 which stores the dispensing pipette tips 201 and the perforating pipette tip 202 together.

The reagent cartridge 100 includes: a main body 101 which is formed in a box shape having an opening; and a hook portion 102 which is formed so as to project laterally from the outer surface of the main body 101. The hook portion 102 is used for fixing the reagent cartridge 100 to the test sample introduction portion 40.

Within the main body 101, a sample well (test sample storage portion) 110 into which a test sample such as a biological sample is put, a reagent well portion 120 in which the reagents for extracting a nucleic acid from a test sample, and the like are stored, a waste liquid well (waste liquid storage portion) 130 into which an unnecessary solution separated in a step of extracting a nucleic acid from a test sample is discarded, and a collection well 140 in which a nucleic acid extracted from a test sample is collected are integrally provided. In addition, the reagent cartridge 100 includes an extraction filter cartridge 150 which contains a carrier that adsorbs a nucleic acid. In the reagent cartridge 100, a holding portion 160 in which the extraction filter cartridge 150 is stored is provided.

The reagent well portion 120 includes a plurality of reagent well (reagent storage portions) 121, 122, 123, 124, 125, and 126, an oil well (oil storage portion) 127, and an oil removal portion 128. In addition, at the reagent well portion 120, the openings of the plurality of reagent wells 121 to 126 and the opening of the oil well 127 are sealed by a sealing film 104 shown in FIG. 2. Entry of gas into the reagent wells 121 to 126 and the oil well 127 is suppressed by the sealing film 104. The sealing film 104 is formed from a material that is allowed to be pierced by the later-described dispensing pipette tips 201. The sealing film 104 can be formed from, for example, a metallic thin film, a plastic film, or the like.

A dissolving liquid 121A which dissolves biological materials such as a cell membrane, a dissolving liquid 122A which dissolves biological materials such as cytoplasm which are not completely dissolved by the dissolving liquid 121A and cause clogging in the carrier, cleaning liquids 123A and 124A for washing away unnecessary matter other than a nucleic acid adsorbed on the carrier, an eluent 125A which elutes a nucleic acid from the carrier, and a diluent 126A for adjusting the concentration of the nucleic acid in an eluate are stored in the reagent wells 121, 122, 123, 124, 125, and 126, respectively.

For example, a well-known oil 127A which is to be layered on a reaction solution in a PCR reaction when being used is stored in the oil well 127. For example, a mineral oil, a silicon oil, or the like can be suitably used as the oil 127A.

The oil removal portion 128 is used for removing the oil 127A that is attached to the outer surface of the dispensing pipette tip 201 when the oil 127A is supplied to the nucleic acid analysis chip 20, and includes therein a filter which is not shown.

The waste liquid well 130 is a recess portion which has a shape corresponding to the outer shape of a bottom portion of the extraction filter cartridge 150 and is able to support the extraction filter cartridge 150. In a state where the extraction filter cartridge 150 is mounted in the waste liquid well 130, the extraction filter cartridge 150 is configured to not fall down within the reagent cartridge 100.

The collection well 140 is a recess portion having such a shape as to be able to support the extraction filter cartridge 150 similarly to the waste liquid well 130. A bottom portion of the collection well 140 has such a shape as to be able to store a nucleic acid solution eluted from the carrier of the extraction filter cartridge 150 by the eluent 125A.

The waste liquid well 130 and the collection well 140 are provided in a positional relation where the waste liquid well 130 and the collection well 140 are adjacent to each other within the reagent cartridge 100. This arrangement is for shortening a path of movement of the extraction filter cartridge 150 when the extraction filter cartridge 150 is moved to the collection well 140 after the extraction filter cartridge 150 is washed at the waste liquid well 130. Thus, it is possible to reduce the possibility that the extraction filter cartridge 150 passing above the reagent cartridge 100 contaminates the reagent cartridge 100 or the like.

The extraction filter cartridge 150 includes therein an extraction filter unit (not shown). The extraction filter unit is used for temporarily adsorbing a nucleic acid contained in a sample dispensed from the sample well 110.

A sealing film 103 is provided to the main body 101 so as to seal the entire opening as shown in FIG. 2. The sealing film 103 is peeled off when the nucleic acid purification kit 10 is used. The sealing film 103 can effectively prevent: the extraction filter cartridge 150 or the like disposed within the main body 101 from dropping from the main body 101; and foreign matter such as dust from being incorporated into the main body 101. It should be noted that the sealing film 103 covering the opening of the reagent cartridge 100 is not indispensable and may not be provided.

The pipette tip rack 200 stores the plurality of dispensing pipette tips 201 and the perforating pipette tip 202. Each dispensing pipette tip 201 is used for dispensing or stirring a liquid stored in the reagent cartridge 100. The liquid stored in the reagent cartridge 100 is dispensed or stirred with any one of the plurality of dispensing pipette tips 201, and cross contamination between liquids does not occur by the dispensing pipette tips 201. Meanwhile, the perforating pipette tip 202 is used for piercing the sealing film 104, which seals the openings of the reagent wells 121 to 126 and the opening of the oil well 127, to make holes. After the holes are made in the sealing film 104 above the respective wells by using the perforating pipette tip 202, the dispensing pipette tips 201 are inserted into the respective wells through the holes.

In addition, the pipette tip rack 200 is also a container for collecting the used dispensing pipette tips 201 and the used perforating pipette tip 202. After the dispensing pipette tips 201 are used in the nucleic acid analyzer 1, the dispensing pipette tips 201 can be discarded as infectious waste together with the pipette tip rack 200. It should be noted that the pipette tip rack 200 is mounted on the stage 41 together with the reagent cartridge 100.

<3. Detailed Configuration of Purification Treatment Portion>

Referring to FIG. 1 again, the purification treatment portion 50 includes: the robot hand 51; the dispensing head 52 which transfers each dispensing pipette tip 201 disposed in the pipette tip rack 200 and sucks, retains, and discharges a liquid by using each dispensing pipette tip 201; and the pressurizing portion 53 which causes air to flow into the extraction filter cartridge 150 through an upper end of the extraction filter cartridge 150 stored in the reagent cartridge 100, to pressurize the inside of the extraction filter cartridge 150.

The robot hand 51 takes the extraction filter cartridge 150 out of the holding portion 160 and places the extraction filter cartridge 150 on the waste liquid well 130. In addition, the robot hand 51 moves the extraction filter cartridge 150 placed on the waste liquid well 130, onto the collection well 140.

The dispensing head 52 corresponds to a dispensing device which performs a dispensing operation by using the dispensing pipette tips 201. The dispensing head 52 is movable in an X axis direction and a Z axis direction by the transfer mechanism which is not shown. Each of the dispensing pipette tips 201 and the perforating pipette tip 202 is detachably connected to the dispensing head 52 by press-in. The dispensing head 52 performs a dispensing operation or transfer of each liquid in a state where each dispensing pipette tip 201 is mounted thereon. In addition, a plurality of the dispensing pipette tips 201 are prepared, and are replaced as appropriate in terms of prevention of contamination. In replacing the dispensing pipette tip 201, an upper end of the dispensing pipette tip 201 is pressed down with a release portion (not shown), whereby the dispensing pipette tip 201 can be released from the dispensing head 52.

The pressurizing portion 53 is hermetically engageable with the extraction filter cartridge 150 and pressurizes the inside of the extraction filter cartridge 150 to extract a liquid.

<4. Details of Dispensing Process>

Figure 4:
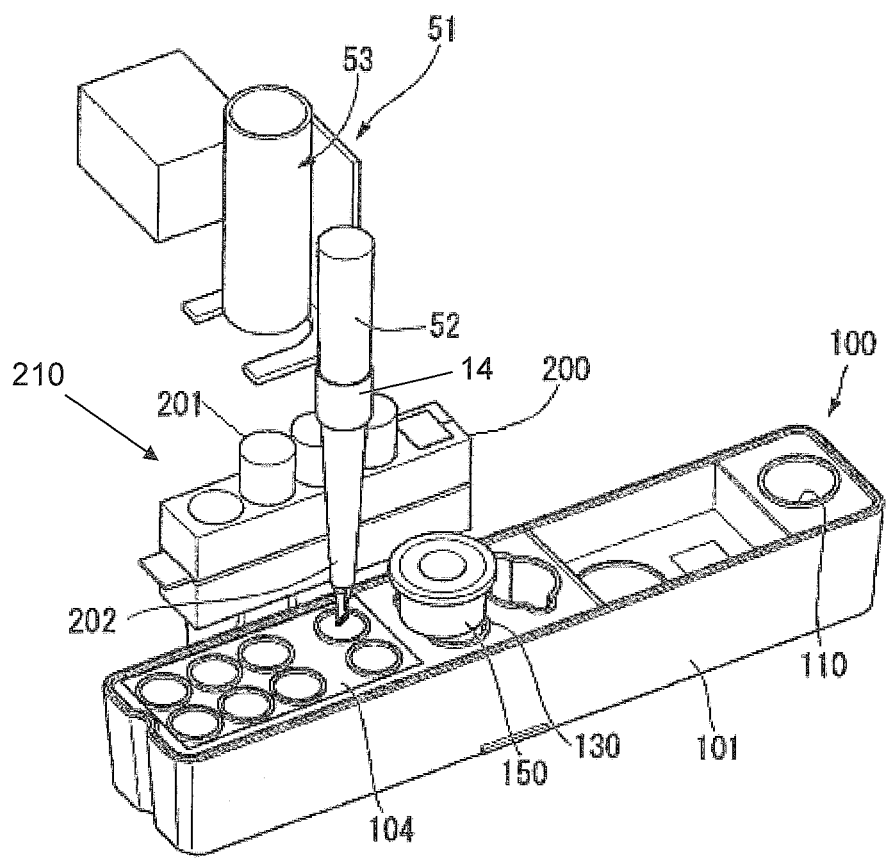
FIG. 4 is a perspective view for explaining the details of a dispensing process.

FIG. 4 is a perspective view for explaining the details of a dispensing process. FIG. 4 shows a state where the extraction filter cartridge 150 is placed on the waste liquid well 130 by using the robot hand 51.

Before the nucleic acid analyzer 1 is actuated, first, for example, a whole blood sample is injected into the sample well 110 of the reagent cartridge 100 manually by a user. In the case where the sealing film 103 shown in FIG. 2 is provided to the reagent cartridge 100, the sealing film 103 is removed manually by the user. Subsequently, the user places the reagent cartridge 100 and the pipette tip kit 210 on the stage 41 as shown in FIG. 1. At that time, the hook portion 102 provided to the reagent cartridge 100 is engaged with the engaged portion 43 of the stage 41, whereby the reagent cartridge 100 is fixed and positioned with respect to the stage 41. In addition, the nucleic acid analysis chip 20 is placed on the analysis chip holder 42 manually by the user.

First, in order to perforate the sealing film 104 by using the perforating pipette tip 202, the transfer mechanism, which is not shown, moves the dispensing head 52 in the X axis direction and moves the stage 41 on which the pipette tip rack 200 has been mounted, in the Y axis direction such that the dispensing head 52 is disposed directly above the perforating pipette tip 202 stored in the pipette tip rack 200. Next, the transfer mechanism moves the dispensing head 52 in a Z axis negative direction to insert the dispensing head 52 into a mount portion 14 of the perforating pipette tip 202. By so doing, the perforating pipette tip 202 is fixed to the dispensing head 52.

Next, the transfer mechanism moves the dispensing head 52 in a Z axis positive direction to take the perforating pipette tip 202 out of the pipette tip rack 200, then moves the dispensing head 52 and the stage 41 in the X axis direction and the Y axis direction, respectively, to directly above any of the wells provided in the reagent cartridge 100.

Next, the transfer mechanism moves the dispensing head 52 in the Z axis negative direction to pierce the sealing film 104 with a leading end portion of the perforating pipette tip 202 to form an opening. After completion of the perforation process, the transfer mechanism moves the dispensing head 52 in the X axis direction and the Z axis direction and also moves the stage 41 in the Y axis direction such that the perforating pipette tip 202 is stored in the pipette tip rack 200. The perforating pipette tip 202 is removed from the dispensing head 52 by using the release portion which is not shown.

In order to efficiently perform an automatic analysis process, the above-described perforation process is preferably performed continuously with respect to all the wells by using the one perforating pipette tip 202 before treatment and analysis of a specimen. In this case, the dispensing head 52 performs perforation with respect to each of the reagent wells 121 to 126 and the oil well 127, which are provided in the reagent cartridge 100, in a predetermined order by using the one perforating pipette tip 202.

After the sealing film 104 is perforated by using the perforating pipette tip 202, the transfer mechanism moves the dispensing head 52 and the stage 41 as appropriate to repeatedly perform mounting of the dispensing pipette tips 201 to the dispensing head 52, movement of the dispensing pipette tips 201 to above the reagent wells 121 to 126, movement of the dispensing pipette tips 201 to above the extraction filter cartridge 150, dismounting of the used dispensing pipette tips 201, and storing of the used dispensing pipette tips 201 into the pipette tip rack 200. It should be noted that the dispensing head 52 performs depressurization and pressurization to suck the reagent into each dispensing pipette tip 201 and discharge the reagent from each dispensing pipette tip 201. The dispensing head 52 dispenses the whole blood sample stored in the sample well 110 and each of the liquids stored in the reagent wells 121 to 126 and the oil well 127, into the extraction filter cartridge 150 in a predetermined order. By so doing, cells in the whole blood sample supplied to the sample well 110 are dissolved and a nucleic acid solution containing a nucleic acid is extracted.

<5. Configuration of Perforating Pipette Tip>

Hereinafter, the perforating pipette tip according to the present embodiment will be described.

Figure 5:
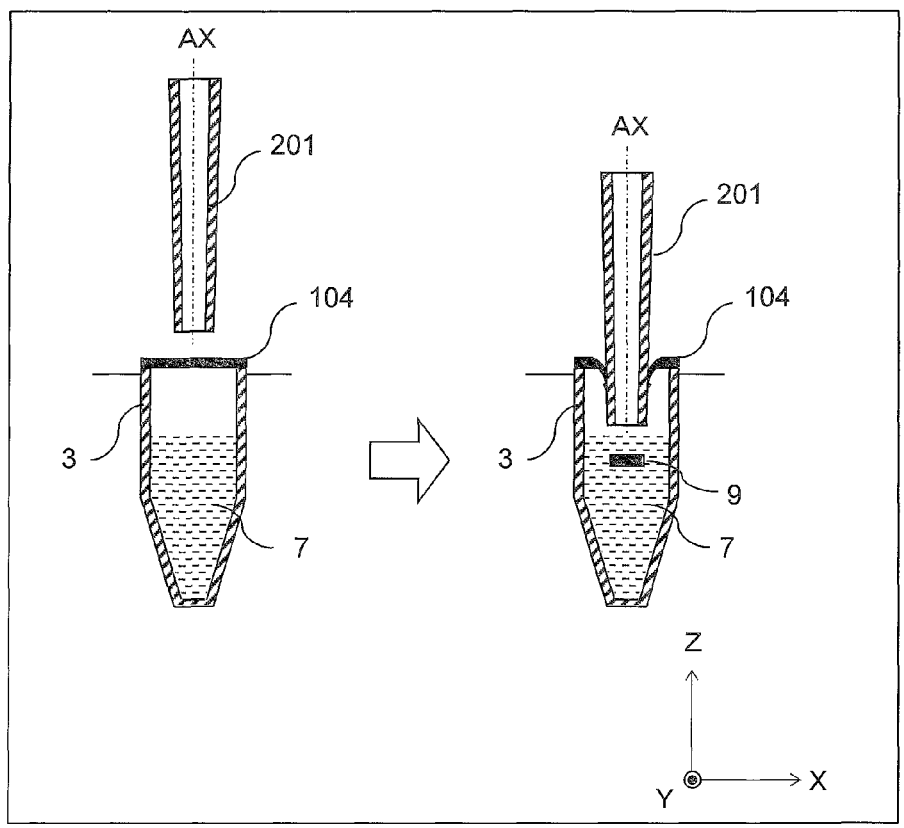
FIG. 5 is an explanatory diagram showing a situation in which a sealing film covering a well of a reagent cartridge is perforated by using an ordinary dispensing pipette tip.

FIG. 5 is an explanatory diagram showing a situation in which a sealing film covering a well of a reagent cartridge by using an ordinary dispensing pipette tip. FIG. 5 shows a cross-sectional view taken along a plane including a central axis AX of the dispensing pipette tip 201. In the following description, the respective wells provided in the above-described reagent cartridge 100 are collectively referred to as "well 3", and the reagents and the like stored in the respective wells are collectively referred to as "liquid 7".

The ordinary dispensing pipette tip 201 is a resin molded product, and its leading end portion is often thinned in order to allow a liquid to be accurately sucked and discharged. In addition, a metal layer or a resin layer having excellent moisture barrier properties is provided to the sealing film 104 covering the well 3 of the reagent cartridge 100, in order to prevent evaporation or contamination of the liquid 7 stored in the well 3 of the reagent cartridge 100. Therefore, in perforating the sealing film 104 covering the well 3 of the reagent cartridge 100 by using the ordinary dispensing pipette tip 201, the sealing film 104 cannot be pierced unless the leading end of the dispensing pipette tip 201 is pressed against the sealing film 104 covering the well 3, with a great propulsive force in the Z axis direction. In addition, a hole in a leading end portion of the ordinary dispensing pipette tip 201 is formed in a perfect circle shape (circular shape) having an inner diameter of about several hundred micrometers in order to allow the reagent to be smoothly sucked and discharged therethrough. Therefore, in perforating the sealing film 104 by using the dispensing pipette tip 201, a portion of the sealing film 104 may be punched out into a circular shape by the leading end portion of the dispensing pipette tip 201, and the punched-out fragment 9 of the sealing film 104 may drop into the well 3 of the reagent cartridge 100.

When the liquid 7 in the well 3 is sucked by using the dispensing pipette tip 201, the fragment 9 punched out by the dispensing pipette tip 201 may be sucked to narrow a flow path of the dispensing pipette tip 201 or be clogged in the dispensing pipette tip 201, which leads to hindering the liquid 7 from being sucked and discharged in a precise amount. In addition, when the dispensing pipette tip 201 discharges the sucked liquid 7, there is also the possibility that the fragment 9 is discharged together with the liquid 7. If foreign matter such as the fragment 9 is introduced into a reaction system, the foreign matter can finally lead to reaction inhibition, and thus this is a big problem.

Figure 6:
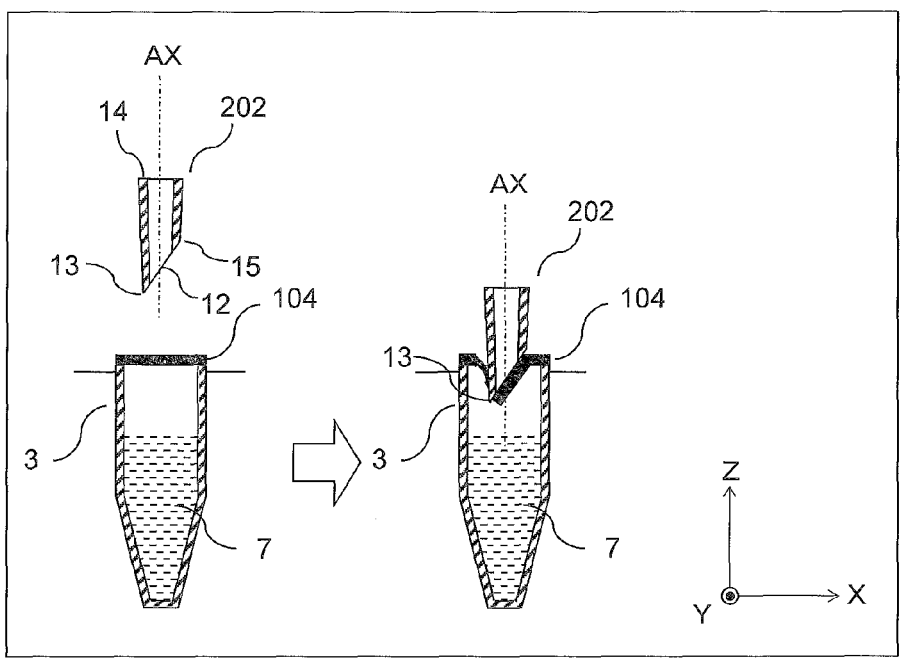
FIG. 6 is an explanatory diagram showing a situation in which a sealing film covering a well of a reagent cartridge is perforated by using a dispensing pipette tip whose leading end has been subjected to cutting.

FIG. 6 is an explanatory diagram showing a situation in which a sealing film covering a well of a reagent cartridge is perforated by using a dispensing pipette tip whose leading end portion has been subjected to cutting.

The perforating pipette tip 202 used in the present embodiment has a leading end surface 12 inclined relative to a central axis AX of the perforating pipette tip 202 which is indicated by an alternate long and short dash line. In the following description, a point that is a point on the outer periphery of the leading end surface 12 and is located at the frontmost side is referred to as "leading end surface lowermost portion 13". In addition, a point that is a point on the outer periphery of the leading end surface 12 and is located at the side closest to the mount portion 14 is referred to as "leading end surface uppermost portion 15". In the perforating pipette tip 202, a portion at and near the leading end surface lowermost portion 13 is incisive as compared to the ordinary dispensing pipette tip 201, and thus is able to perforate the sealing film 104 with a smaller propulsive force in the Z axis direction than that when the sealing film 104 is perforated by using the ordinary dispensing pipette tip 201. Therefore, a load on a mechanism which creates a propulsive force in the Z axis direction of the perforating pipette tip 202 is reduced, and it is possible to lengthen the life of consumable components used in the mechanism.

In addition, when the leading end surface 12 is formed so as to be inclined relative to the central axis AX as in the perforating pipette tip 202 according to the present embodiment, occurrence of a fragment of the sealing film 104 at the time of perforation can also be suppressed. In other words, in perforating the sealing film 104, the leading end surface lowermost portion 13 of the perforating pipette tip 202 penetrates through the sealing film 104, and then cutting of the sealing film 104 proceeds with downward movement of the perforating pipette tip 202. However, at and near the leading end surface uppermost portion 15, an angle formed between the leading end surface 12 and the outer surface of the perforating pipette tip 202 is an obtuse angle, and thus the sealing film 104 is not completely cut by the leading end surface uppermost portion 15. As a result, the cut portion of the sealing film 104 is not separated and remains even after the perforation.

After the sealing film 104 is perforated by using the perforating pipette tip 202 according to the present embodiment, the perforating pipette tip 202 is replaced with the dispensing pipette tip 201 having an ordinary shape. Then, the leading end of the ordinary dispensing pipette tip 201 is inserted into the well 3 through the formed opening and the liquid 7 in the well 3 is sucked.

The perforating pipette tip 202 according to the present embodiment can be produced by obliquely cutting a leading end of a commercially-available dispensing pipette tip 201 for biology and biochemistry. The perforating pipette tip 202 is producible by only simply cutting the ordinary dispensing pipette tip 201 with a sharp knife, and it is possible to minimize thus the cost required for the production. It should be noted that the perforating pipette tip 202 having the leading end surface 12 inclined relative to the central axis AX may be produced by ordinary plastic molding.

Figure 7:
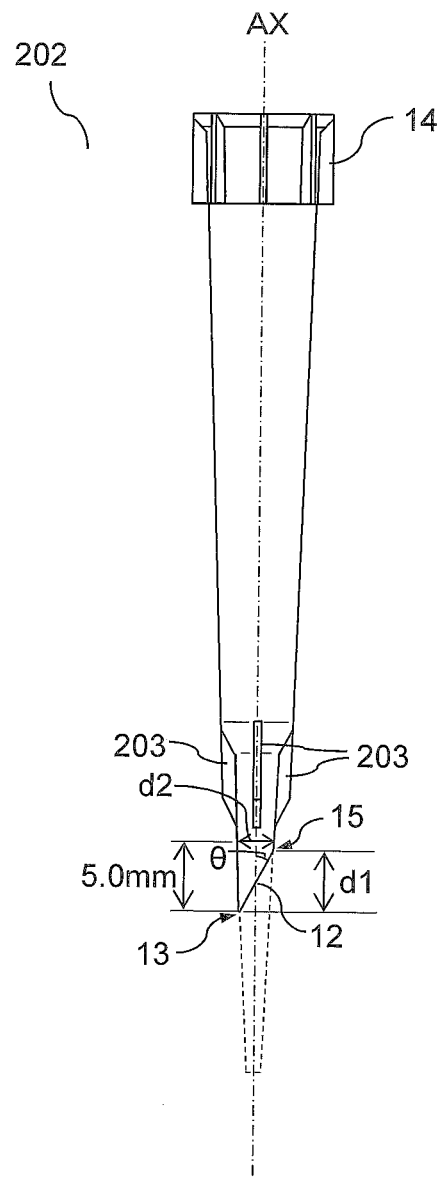
FIG. 7 is a diagram showing the detailed shape of the perforating pipette tip shown in FIG. 6.

FIG. 7 is a diagram showing the detailed shape of the perforating pipette tip shown in FIG. 6. In FIG. 7, a portion that is cut and removed from an ordinary dispensing pipette tip is indicated by a broken line.

An ordinary dispensing pipette tip has a tapered shape which is tapered toward its leading end. Therefore, when the leading end surface 12 is formed by curing a portion of the dispensing pipette tip at the leading end side, the leading end surface 12 is formed in a portion having a relatively large outer diameter as compared to the leading end of the dispensing pipette tip 201. Thus, a hole formed in the perforating pipette tip 202 is also large in size. If a larger hole can be formed in the sealing film 104 of the reagent cartridge 100, the ordinary dispensing pipette tip 201 is easily inserted into the well 3 through the formed opening at the time of dispensing. In addition, since an inflow path for causing air to flow into the well 3 during suction of the liquid 7 can be made large, it is possible to accurately suck the liquid 7 in a shorter time.

Here, the shape of the leading end surface of the perforating pipette tip 202 will be described.

An angle $\theta$ of the leading end surface 12 relative to the central axis AX of the perforating pipette tip 202 is preferably not lower than 15° and not higher than 35°. If the angle $\theta$ is lower than 15°, the strength of a portion at and near the leading end surface lowermost portion 13 is excessively decreased. Thus, in piercing the sealing film 104, the portion at and near the leading end surface lowermost portion 13 may deform due to the strength of the sealing film 104. In addition, if the angle $\theta$ exceeds 35°, a propulsive force in the Z axis direction required to perforate the sealing film 104 (a force required for perforation) is nearly equal to that in the case with the ordinary dispensing pipette tip 201. As a result, it is difficult to easily perforate the sealing film 104.

In addition, the height of the leading end surface 12 in a direction parallel to the central axis AX of the perforating pipette tip 202, namely, a level difference $d1$ between the leading end surface lowermost portion 13 and the leading end surface uppermost portion 15 in the direction parallel to the central axis AX, is set in a range of not smaller than 4.0 mm and not larger than 7.5 mm. If the level difference d1 between the leading end surface lowermost portion 13 and the leading end surface uppermost portion 15 is smaller than 4.0 mm, the opening in the leading end surface 12 is excessively large, and the amount of the liquid attached to the opening portion at the leading end of the perforating pipette tip 202 when the perforating pipette tip 202 penetrates through the sealing film 104 is increased. In this case, when the sealing film 104 is continuously perforated above a plurality of the wells 3, contamination between the wells by the liquid attached to the leading end of the perforating pipette tip 202 cannot be neglected, and thus it is not preferred that the level difference d1 is smaller than 4.0 mm. In addition, it is also conceivable that the attached liquid drips from the leading end to contaminate the reagent cartridge 100 when the perforating pipette tip 202 is moved, and thus it is not preferred that the level difference d1 is smaller than 4.0 mm. On the other hand, if the level difference d1 between the leading end surface lowermost portion 13 and the leading end surface uppermost portion 15 exceeds 7.5 mm, when an amount by which the perforating pipette tip 202 moves downward in the Z axis direction is set such that an amount of the liquid entering into the leading end surface of the perforating pipette tip 202 does not become excessive, the leading end surface 12 cannot completely penetrate through the sealing film 104. In this case, the size of a formed hole is determined by the outside dimension at an intermediate position of the leading end surface 12. Thus, the size of the formed hole is reduced as compared to the case where the leading end surface 12 penetrates through the sealing film 104. Therefore, it is not preferred that the level difference d1 between the leading end surface lowermost portion 13 and the leading end surface uppermost portion 15 exceeds 7.5 mm. The level difference d1 between the leading end surface lowermost portion 13 and the leading end surface uppermost portion 15 is more preferably not smaller than 5.0 mm and not larger than 7.5 mm, among the above range. In this case, it is possible to sufficiently increase the size of the formed hole while the amount of the liquid 7 attached to the perforating pipette tip 202 is reduced.

In addition, a maximum value d2 of the outside dimension in the radial direction at a position away from the leading end surface lowermost portion 13 of the perforating pipette tip 202 in the central axis AX direction by 5.0 mm is preferably higher than 1.6 mm. In the case where the sealing film 104 is perforated by using the ordinary dispensing pipette tip 201, when the leading end of the dispensing pipette tip 201 is moved downward from the upper surface of the sealing film 104 in the Z axis negative direction by about 5.0 mm, the dispensing pipette tip 201 completely penetrates through the sealing film 104 to form an opening. The dimension of the opening formed when the ordinary dispensing pipette tip 201 is used is 1.6 mm Therefore, if the value d2 is set to be higher than 1.6 mm, when an amount by which the pipette tip is inserted into the well 3 at the time of perforation is constant, it is possible to increase the size of an opening formed by the perforating pipette tip 202 as compared to the case where perforation is performed by using the ordinary dispensing pipette tip 201.

As described above, when the perforating pipette tip 202 according to the present embodiment is used, it is possible to form a larger hole in the sealing film 104 than in the case where perforation is performed with the leading end of the ordinary dispensing pipette tip 201. In addition, since occurrence of a fragment of the sealing film 104 at the time of dispensing the reagent is suppressed, it is possible to reduce the possibility that suction of the reagent is hindered by a fragment of the sealing film 104 or a fragment of the cut sealing film 104 is incorporated into the reaction system. Furthermore, in the perforating pipette tip 202 according to the present embodiment, when the shape of the leading end surface 12 is designed such that at least one of the above conditions is met, it is possible to reduce the amount of the liquid attached to the leading end surface 12. Therefore, even in the case where a sealing film is continuously perforated above a plurality of wells, it is possible to suppress contamination of the reagent between the wells.

The perforating pipette tip 202 according to the present embodiment is producible by cutting a portion of a leading end portion of the ordinary dispensing pipette tip 201, and thus it is possible to minimize the cost required for the production. In this case, the shape of the cut surface of the ordinary dispensing pipette tip 201 is designed such that at least one of the above conditions is met.

Hereinafter, a method for further increasing the size of a hole formed in the sealing film 104, by using the perforating pipette tip 202 according to the present embodiment, will be described.

As a first method, there is a method in which after the perforating pipette tip 202 is stuck into the sealing film 104, the perforating pipette tip 202 is moved in the X axis direction or the Y axis direction, thereby increasing the size of a formed hole. In this case, in order to further increase the size of the formed hole, the perforating pipette tip 202 is more preferably moved in both in the X axis direction and the Y axis direction.

As a second method, there is a method in which after the perforating pipette tip 202 is stuck into the sealing film 104, the reagent cartridge 100 is moved in the X axis direction or the Y axis direction, thereby increasing the size of a formed hole. In this case, in order to further increase the size of the formed hole, the reagent cartridge 100 is more preferably moved in both in the X axis direction and the Y axis direction.

As a third method, there is a method in which after the perforating pipette tip 202 is stuck into the sealing film 104, both the perforating pipette tip 202 and the reagent cartridge 100 are moved in different directions, thereby increasing the size of a formed hole. In this case, for example, the perforating pipette tip 202 may be moved in either one of the X axis direction and the Y axis direction, and the reagent cartridge 100 may be moved in the other of the X axis direction and the Y axis direction.

When the perforating pipette tip 202 according to the present embodiment and any one of the first to third methods as described above are used in combination, it is possible to further increase the size of a hole as compared to the case where only the perforating pipette tip 202 is used.

In the case where the hole enlargement process by the above first to third methods is performed, ribs 203 as shown in FIG. 7 are preferably provided to the outer surface of the perforating pipette tip 202. Each rib 203 is formed so as to project outward in the radial direction of the perforating pipette tip 202 on a plane including the central axis AX of the perforating pipette tip 202. Each rib 203 is provided at a position away from the leading end surface uppermost portion 15 of the perforating pipette tip 202 by a fixed distance.

In the case where the perforating pipette tip 202 provided with the ribs 203 is used, after the leading end of the perforating pipette tip 202 is stuck into the sealing film 104, the perforating pipette tip 202 is further moved downward such that the ribs 203 penetrate through the sealing film 104. Then, in a state where the ribs 203 penetrate through the sealing film 104, the perforating pipette tip 202 is moved horizontally relative to the reagent cartridge 100 by any one of the above first to third methods. When the perforating pipette tip 202 provided with the ribs 203 is used, it is possible to easily and efficiently increase the size of a hole formed with the leading end of the perforating pipette tip 202.

It should be noted that the number of the ribs 203 may be any number that is not smaller than 1. In the case where the number of the ribs 203 is not smaller than 2, the ribs 203 are preferably provided at equal intervals in the radial direction in order to allow a hole to be efficiently enlarged. In the example of FIG. 7, for example, the four ribs 203 are radially provided at equal intervals in the radial direction, namely, provided such that a cross shape is formed when being viewed from the central axis AX.

The hole enlargement process by the above first to third methods may be performed, for example, with respect to a specific well that is used for stirring a sample and a reagent. Specifically, the reagent well 121 on the reagent cartridge 100 shown in FIG. 3 is used for stirring a whole blood sample injected therein and the dissolving liquid 121A stored therein at an initial stage of a nucleic acid extraction process. Bubbles are easily generated when the whole blood sample and the dissolving liquid 121A are stirred. Thus, when a large hole is previously formed, air easily comes out of the reagent well 121 at the time of injecting the sample into the reagent well 121. As a result, it is possible to suppress overflow of the stirred sample. In addition, the sample is stirred by inserting the dispensing pipette tip 201 used for injecting the sample, into the reagent well and moving the dispensing pipette tip 201 horizontally relative to the reagent well 121. When the size of the hole formed with the leading end of the perforating pipette tip 202 is previously increased, it is possible to efficiently perform the stirring process by using the dispensing pipette tip 201.

In the case where the hole enlargement process is performed with respect to a specific well by using the perforating pipette tip 202 provided with the ribs 203 as in the example of FIG. 7, an amount by which the perforating pipette tip 202 is moved downward is increased due to the necessity to cause the ribs 203 to penetrate through the sealing film 104. Thus, in order to suppress contamination of the reagent, it is preferred that after perforation is performed sequentially with respect to wells for which the hole enlargement process is not necessary, perforation and the hole enlargement process are finally performed with respect to a well for which the hole enlargement process is necessary.

It should be noted that in the above-described embodiments, the nucleic acid analyzer has been described as an example of an automatic analyzer including a dispensing device, but the above-described pipette tip set and perforating method are also applicable to various apparatuses which dispense a liquid by using a pipette tip, other than a nucleic acid analyzer.

In addition, in the above-described embodiments, as a reagent cartridge, the reagent cartridge in which the reagents for nucleic acid extraction are enclosed and the analyzer using the reagent cartridge have been described as an example, but the above-described pipette tip set and perforating method are also applicable to a cartridge in which various reagents for biochemical analysis other than for nucleic acid extraction, such as for protein analysis or for antibody analysis, and an analyzer using the cartridge.

Furthermore, in the above-described embodiments, the pipette tip set has been described in which the dispensing pipette tips and the perforating pipette tip are stored together in the pipette tip rack and which is supplied in the form of being enclosed in a package for the purpose of preventing contamination and the like before use, but the perforating pipette tip may be supplied alone.

Furthermore, in the above-described embodiments, the case has been described in which the dispensing head is movable in the X axis direction and the Z axis direction and the stage is movable in the Y axis direction. However, the combination of the directions in which the dispensing head and the stage are moved may be any combination as long as the dispensing head and the stage are movable relative to each other to a position at which a dispensing operation is enabled. For example, either one of the dispensing head and the stage may be configured to be fixed, and the other of the dispensing head and the stage may be configured to be movable in the X axis, Y axis, and Z axis directions. In addition, as another example, the dispensing head may be configured to be movable in the X axis, Y axis, and Z axis directions, and the stage may be configured to be movable in one or both of the X axis direction and the Y axis direction.

EXAMPLES

Hereinafter, examples in which the perforating pipette tips according to the above-described embodiments were more specifically implemented will be described.

Figure 8:
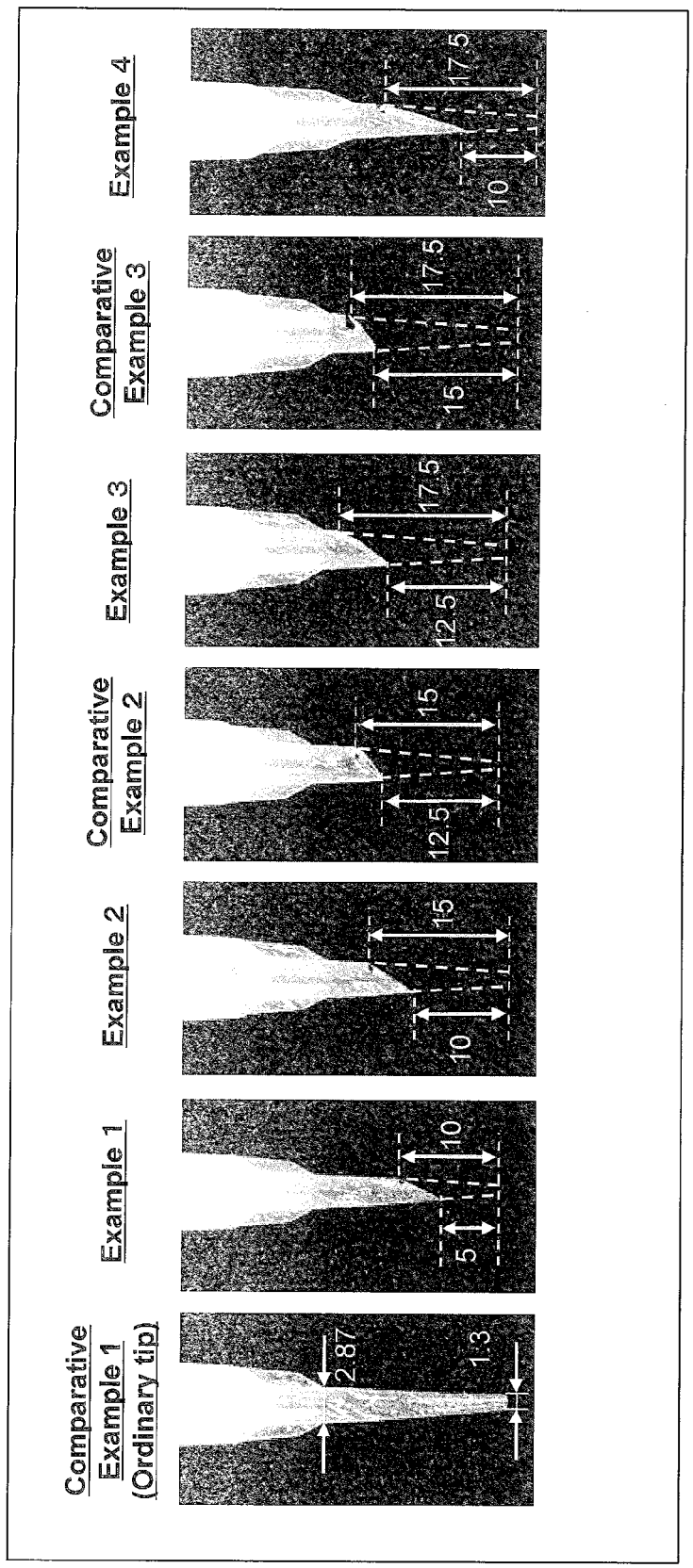
FIG. 8 is a diagram showing the shapes of perforating pipette tips according to Examples 1 to 4 and Comparative Examples 1 to 3.

FIG. 8 is a diagram showing the shapes of perforating pipette tips according to Examples 1 to 4 and Comparative Examples 1 to 3. In Comparative Example 1, an ordinary dispensing pipette tip was used as the perforating pipette tip. In addition, in Examples 1 to 4 and Comparative Examples 2 and 3, a portion indicated by a broken line represents a portion that was cut and removed from an ordinary dispensing pipette tip. In addition, in Examples 1 to 4 and Comparative Examples 2 and 3, a value shown at the left side of each perforating pipette tip is the distance (mm) in the central axis direction from the leading end of the ordinary dispensing pipette tip to the leading end surface lowermost portion, and a value shown at the right side of each perforating pipette tip is the distance (mm) in the central axis direction from the leading end of the ordinary dispensing pipette tip to the leading end surface uppermost portion. It should be noted that the leading end portion of the ordinary dispensing pipette tip had a forward tapered shape, the outer diameter of the leading end portion was 1.3 mm, and the outer diameter of a portion where ends of the ribs (a portion indicated by arrows in FIG. 8) are connected was 2.87 mm.

Table 1 shows the results of using each of the perforating pipette tips according to Examples 1 to 4 and Comparative Examples 1 to 3 in a nucleic acid analyzer and perforating a sealing film of a reagent cartridge.

TABLE 1

| Evaluation items | Comparative Example 1 | Example 1 | Example 2 | Comparative Example 2 | Example 3 | Comparative Example 3 | Example 4 |
|---|---|---|---|---|---|---|---|
| Size of hole formed in sealing film | 1.60 | 2.04 | 2.51 | 2.74 | 2.90 | 3.31 | 2.38 |

TABLE 1-continued

| Evaluation items | Comparative Example 1 | Example 1 | Example 2 | Comparative Example 2 | Example 3 | Comparative Example 3 | Example 4 |
|---|---|---|---|---|---|---|---|
| Easiness of perforation (displacement amount from reference position [mm]) | Δ (±0) | ◯ (−0.3) | ◯ (−0.3) | Δ (±0) | Δ (±0) | X (+0.2) | ◯ (−0.2) |
| Amount of attached liquid | Small | Small | Intermediate | Large | Intermediate | Large | Small |
| Risk of drop of film fragment | 19% | 0% | 0% | 0% | 0% | 0% | 0% |

The methods for evaluating the evaluation items shown in the leftmost column of Table 1 are as follows.

The size (mm) of a hole formed in the sealing film was measured by: capturing an image of an opening formed in the sealing film of the reagent cartridge by using a perforating pipette tip; and performing image analysis by using microscope measurement software.

Easiness of perforation was evaluated as "◯: it is easy to make a hole, Δ: normal, and X: it is difficult to make a hole" on the basis of the position of the dispensing head at the time of seal break. More specifically, perforation was performed by using the perforating pipette tips according to Examples 1 to 4 and Comparative Examples 1 to 3, and a state where the leading end of each perforating pipette tip was inserted to a depth of 5.0 mm from the position of the sealing film was regarded as seal break. In addition, the position of the dispensing head at the time of seal break by using the ordinary dispensing pipette tip (Comparative Example 1) was set as a reference position. The position of the dispensing head at the time of seal break by using each of the perforating pipette tips according to Examples 1 to 4 and Comparative Examples 2 and 3 was obtained, and the difference between the obtained position of the dispensing head and the reference position was regarded as a displacement amount from the reference position. A positive sign of the displacement amount means that an amount by which the dispensing head moved downward was large as compared to the case of using the ordinary dispensing pipette tip (Comparative Example 1), and a negative sign of the displacement amount means that an amount by which the dispensing head moves downward was small as compared to the case of using the ordinary dispensing pipette tip (Comparative Example 1). If the displacement amount from the reference position is negative, a less amount by which the dispensing head moves downward is needed, and thus it can be evaluated that a hole is easily made in the sealing film.

An amount of attached liquid was evaluated by visually observing the amount of the liquid attached to the leading end of the perforating pipette tip.

The risk of drop of a film fragment was calculated as a ratio of the number of times a fragment dropped into a well, relative to the number of times of perforation, when 10 sets of perforation with respect to 6 wells of one reagent cartridge were repeated and presence/absence of a fragment dropped into a well was visually observed.

In the case of using the ordinary dispensing pipette tip according to Comparative Example 1, many cases occurred in which a fragment of the sealing film dropped into the well of the reagent cartridge. In the case of using the perforating pipette tips according to Comparative Examples 2 and 3, the amount of the liquid attached to the leading end was large, and a phenomenon was observed that the liquid blocked the opening portion at the leading end of the perforating pipette tip. In particular, in the case of using the perforating pipette tip according to Comparative Example 3, a situation was also observed in which liquid balls were created at the leading end and burst in air, and it was recognized that the amount of attached liquid was large.

In contrast, in the case of using the perforating pipette tips according to Examples 1 to 4, the size of the hole formed in the sealing film was able to be increased as compared to the case of using the ordinary dispensing pipette tip (Comparative Example 1). In addition, after perforation, drop of a fragment of the sealing film into the well of the reagent cartridge was also not observed. Furthermore, the amount of the liquid attached to the perforating pipette tip after perforation was nearly equal to or larger than that in the case of using the ordinary dispensing pipette tip (Comparative Example 1), but was smaller than that in the case of using the dispensing pipette tips according to Comparative Examples 2 and 3. Therefore, in the case of using the perforating pipette tips according to Examples 1 to 4, it was confirmed that occurrence of contamination between the wells or contamination of the reagent cartridge due to the liquid dropping on the reagent cartridge after perforation can be reduced.

Figure 9:
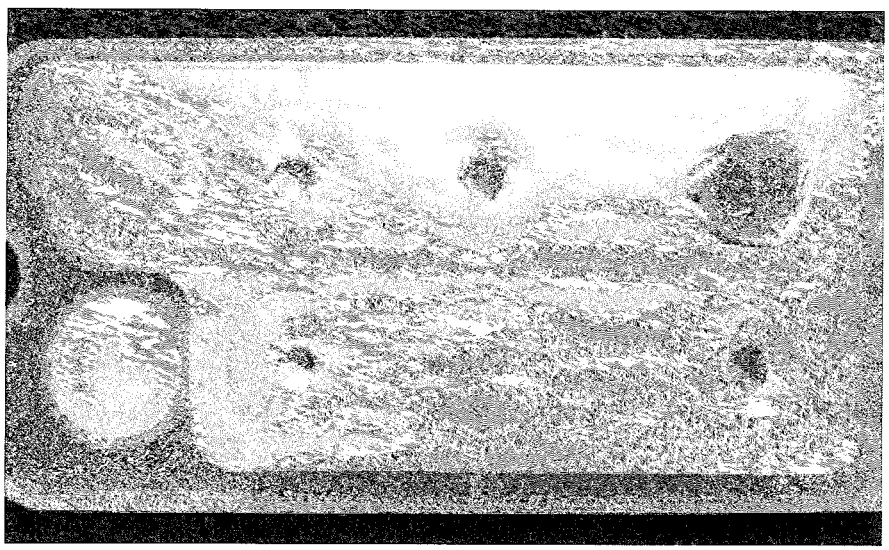
FIG. 9 is a diagram showing a state of a sealing film after the sealing film was perforated by using the perforating pipette tip according to Example 3.
Figure 10:
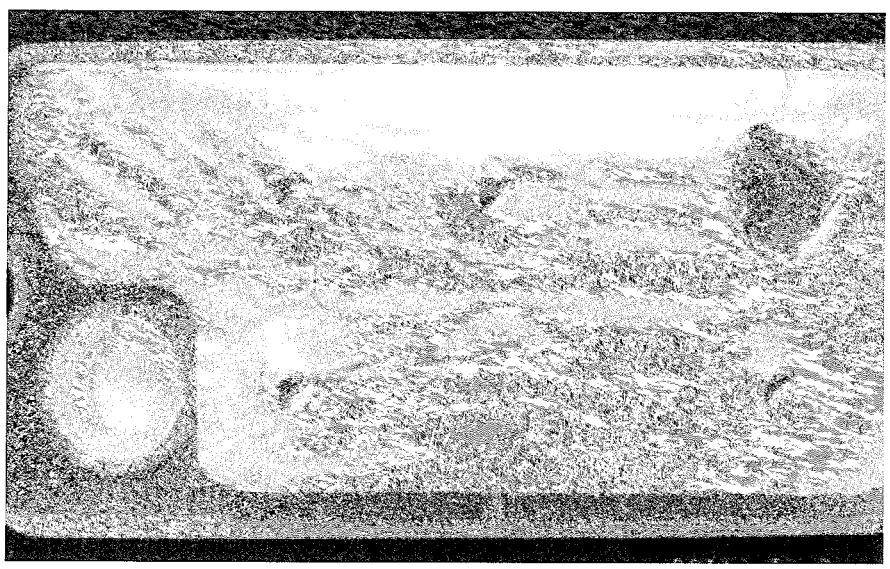
FIG. 10 is a diagram showing a state of a sealing film after the sealing film was perforated by using the perforating pipette tip according to Example 4.

FIG. 9 is a diagram showing a state of the sealing film after the sealing film was perforated by using the perforating pipette tip according to Example 3, and FIG. 10 is a diagram showing a state of the sealing film after the sealing film was perforated by using the perforating pipette tip according to Example 4. In FIGS. 9 and 10, an opening formed in the sealing film above the upper right well was enlarged by horizontally moving the dispensing head in the X axis direction and also moving the stage in the Y axis direction in a state where ribs provided to the perforating pipette tip penetrated through the sealing film. As shown in FIGS. 9 and 10, it was confirmed that the opening formed in the sealing film is sufficiently enlarged by the ribs.

Among Examples 1 to 4, it was confirmed that the perforating pipette tip according to Example 3 is excellent in that the hole formed in the sealing film is the largest. In addition, in the case of performing perforation by using the perforating pipette tip according to Example 3, attachment of the liquid to the leading end of the perforating pipette tip was observed, but an amount of attached liquid that fills the opening portion at the leading end was not observed, and no contamination of the reagent cartridge was observed during 12 tests. Therefore, it was confirmed that the perforating pipette tip according to Example 3 exerts a most superior effect in terms of both the size of a hole that can be formed and a small amount of attached liquid. It should be noted that the inclination angle (θ in FIG. 7) of the leading end surface of the perforating pipette tip according to Example 3 relative to the central axis was 26.7°, the height (d1 in FIG. 7) of the leading end surface in the central axis direction was 5.0 mm, and the maximum value (d2 in FIG. 7) of the outside dimension in the radial direction at a position away from the leading end in the central axis direction by 5.0 mm was 2.74 mm Meanwhile, also in the perforating pipette tip according to Example 4, attachment of the liquid to the leading end was observed, but an amount of attached liquid that fills the opening portion at the leading end was not observed. In addition, in the case of using the perforating pipette tip according to Example 4, the visually observed amount of attached liquid after perforation was the smallest, but contamination of the reagent cartridge was observed once during 8 tests (note that it was after a large hole was formed by deep insertion into the upper right well). Moreover, the size of the hole formed by using the perforating pipette tip according to Example 4 was smaller than that in the case of using the perforating pipette tip according to Example 3. For these reasons, the effects exerted by the perforating pipette tip according to Example 4 were superior to those by the perforating pipette tips according to Comparative Examples 1 to 3 but were second to those by the perforating pipette tip according to Example 3. It should be noted that the inclination angle (θ in FIG. 7) of the leading end surface of the perforating pipette tip according to Example 4 relative to the central axis was 17.8°, the height (d1 in FIG. 7) of the leading end surface in the central axis direction was 7.5 mm, and the maximum value (d2 in FIG. 7) of the outside dimension in the radial direction at a position away from the leading end in the central axis direction by 5.0 mm was 2.74 mm The pipette tip set and the perforating method according to the present disclosure can be used for easily perforating a film for a reagent in a dispensing device included in a test apparatus for biochemical analysis.

While the disclosure has been described in detail, the foregoing description is in all aspects illustrative and not restrictive. It will be understood that numerous other modifications and variations can be devised without departing from the scope of the disclosure.

What is claimed is:

1. A perforating method for perforating a film covering a well provided in a reagent cartridge by using a dispensing device including: a dispensing head configured to suck and discharge a liquid; and a stage configured to support the reagent cartridge in which a reagent for biochemical analysis is enclosed, the perforating method comprising:

mounting a perforating pipette tip on the dispensing head, the perforating pipette tip being formed by cutting a leading end of a pipette tip, that has the same shape as the dispensing pipette tip, along a plane inclined relative to a central axis thereof, and the perforating pipette tip having
    a leading end surface inclined relative to the central axis, and
    on a plane including the central axis, a plurality of ribs that project from an outer surface of the perforating pipette tip in a radial direction of the perforating pipette tip, and are radially arranged at equal intervals in a circumferential direction of the perforating pipette tip;

disposing the leading end of the perforating pipette tip mounted on the dispensing head, perpendicularly above the film;

moving the dispensing head downward to stick the leading end of the perforating pipette tip into a film to form a hole in the film; and enlarging the formed hole by moving at least one of the dispensing head and the cartridge in a horizontal direction and tearing the film in the horizontal direction, in a state where the leading end of the perforating pipette tip is stuck into the film.

2. The perforating method according to claim 1, wherein a height of the leading end surface in a direction parallel to the central axis of the perforating pipette tip is not lower than 4 mm and not higher than 7.5 mm.

3. The perforating method according to claim 1, wherein an angle formed between the central axis and the leading end surface of the perforating pipette tip is not lower than 15° and not higher than 35°.

4. The perforating method according to claim 1, wherein a maximum value of an outside dimension in a radial direction of the perforating pipette tip at a position away from a leading end of the perforating pipette tip set in a direction parallel to the central axis is higher than 1.6 mm.

5. The perforating method according to claim 1,
the method further comprising:
    further moving the dispensing head downward after the leading end of the perforating pipette tip is stuck into the film; and
    enlarging the formed hole by moving at least one of the dispensing head and the cartridge in a horizontal direction and tearing the film in the horizontal direction, in a state where the rib penetrates through the film.

* * * * *